United States Patent [19]

Poss

[11] Patent Number: 5,286,746
[45] Date of Patent: Feb. 15, 1994

[54] SULFUR-SUBSTITUTED MEVINIC ACID DERIVATIVES

[75] Inventor: Kathleen M. Poss, Lawrenceville, N.J.

[73] Assignee: E. R. Squibb & Sons, Inc., Princeton, N.J.

[21] Appl. No.: 811,124

[22] Filed: Dec. 20, 1991

[51] Int. Cl.$^5$ ................................. A61K 31/35
[52] U.S. Cl. .................... 514/460; 514/510; 560/1; 560/10; 560/80; 560/81; 560/105; 560/117; 560/119; 560/122; 560/123; 560/124; 560/125; 560/126; 560/147; 560/152; 560/187; 560/188; 560/256
[58] Field of Search ............. 560/119, 117, 10, 105, 560/122, 125, 1, 231, 256, 80, 81, 123, 124, 126, 147, 152, 187, 188; 549/292; 514/460, 510, 546, 532

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 |
| 4,231,938 | 11/1980 | Monaghan et al. | 260/343.5 |
| 4,346,227 | 8/1982 | Terahara et al. | 560/119 |
| 4,410,629 | 10/1983 | Terahara et al. | 435/146 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 424/279 |

FOREIGN PATENT DOCUMENTS

| | | |
|---|---|---|
| 0065835 | 12/1982 | European Pat. Off. . |
| 0137444 | 4/1985 | European Pat. Off. . |
| 0251625 | 1/1988 | European Pat. Off. . |
| 0306210 | 3/1989 | European Pat. Off. . |
| 0323867 | 7/1989 | European Pat. Off. . |
| 0349063 | 3/1990 | European Pat. Off. . |
| 0415488 | 3/1991 | European Pat. Off. . |
| 2075013A | 11/1981 | United Kingdom . |

OTHER PUBLICATIONS

F. M. Singer et al.; "New Inhibitors of in vitro Conversion of Acetate and Mevalonate to Cholesterol", Proc. Soc. Exper. Biol. Med., 102, 370 (1959).

F. H. Hulcher, "Inhibition of Hepatic Cholesterol Biosynthesis by 3,5-Dihydroxy-3,4,4-trimethylvaleric Acid and its Site of Action", Arch. Biochem. Biophys., 146, 422 (1971).

A. G. Brown et al., "Crystal and Molecular Structure of Compactin, a New Antifungal Metabolite from *Penicillium brevicompactum*", J. Chem. Soc. Perkin I. 1165-1170 (1976).

U.S. patent application Ser. No. 724,272, Jul. 1991.

*Primary Examiner*—Michael L. Shippen
*Attorney, Agent, or Firm*—Timothy J. Gaul

[57] ABSTRACT

Antihypercholesterolemic activity is exhibited by compounds of the formula

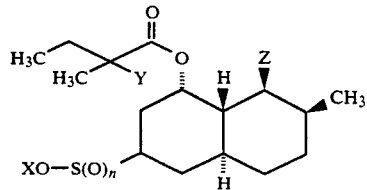

wherein:
X is hydrogen, alkali metal or ammonium;
Y is hydrogen, alkyl, cycloalkyl, aryl, or aralkyl;

Z is

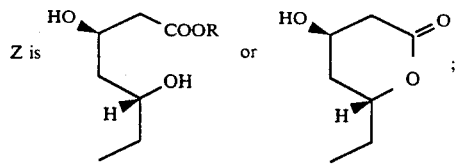

R is hydrogen, alkyl, ammonium, alkylammonium, or alkali metal (such as Na, Li, or K); and
n is 1 or 2.

10 Claims, No Drawings

SULFUR-SUBSTITUTED MEVINIC ACID DERIVATIVES

FIELD OF THE INVENTION

The present invention relates to sulfursubstituted mevinic acid derivatives, which are HMG-CoA reductase inhibitors useful as antihypercholesterolemic agents, and to methods of use for such compounds.

BRIEF DESCRIPTION OF THE INVENTION

In accordance with the present invention, compounds of the formula

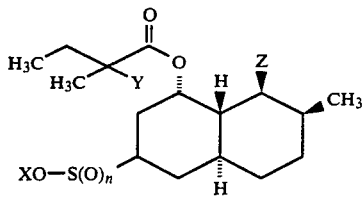

I and pharmaceutically acceptable salts thereof possess activity as HMG-CoA reductase inhibitors, thus making them useful as antihypercholesterolemic agents. In formula I and throughout this specification, the above symbols are defined as follows:

X is hydrogen, alkali metal or ammonium;

Y is hydrogen, alkyl, cycloalkyl, aryl, or aralkyl;

Z is 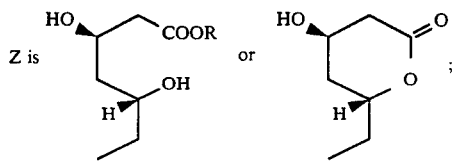

R is hydrogen, alkyl, ammonium, alkylammonium, or alkali metal (such as Na, Li, or K); and n is 1 or 2.

DETAILED DESCRIPTION OF THE INVENTION

Definition of Terms

Listed below are definitions of various terms used to describe this invention. These definitions apply to the terms as they are used throughout this specification (unless otherwise limited in specific instances) either individually or as part of a larger group.

The terms "alkyl", "alk" and "alkylene" include both straight and branched chain radicals of up to 12 carbons, preferably 1 to 8 carbons. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Exemplary alkylene groups are those derived from the foregoing exemplary alkyl groups (e.g., —CH$_2$—, —CH$_2$CH$_2$—). The terms "alkyl", "alk" and "alkylene" also include such groups having halo (such as F, Br, Cl or I or CF$_3$), alkoxy, hydroxy, thio, thioalkyl, aryl, alkyl-aryl, haloaryl, cycloalkyl, or alkylcycloalkyl substituents.

The term "alkenyl" by itself or as part of another group refers to both straight and branched chain groups having at least one double bond. Those groups having 2 to 10 carbon atoms are preferred. The term "alkenyl" further includes groups having halo, alkoxy, aryl, alkyl-aryl, haloaryl, cycloalkyl, or alkylcycloalkyl substituents.

The term "alkynyl" by itself or as part of another group refers to both straight and branched chain groups having at least one triple bond. Those groups having 2 to 10 carbon atoms are preferred. The term "alkynyl" further includes groups having halo, alkoxy, aryl, alkyl-aryl, haloaryl, cycloalkyl, or alkylcycloalkyl substituents.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, wherein such groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl, wherein the substituent on either the phenyl or naphthyl may be 1 or 2 lower alkyl groups, 1 to 5 halogens such as Cl, Br or F (1 to 7 halogens in the case of naphthyl), and/or 1 or 2 lower alkoxy groups.

The term "halogen" or "halo" refers to fluorine, chlorine, bromine and iodine, as well as trifluoromethyl.

The term "acyl" refers to all organic moieties that may be derived from an organic acid (i.e., a carboxylic acid) by exchange of the hydroxyl group; i.e., compounds of the partial formula

wherein R$^1$ is alkyl, aryl, aralkyl, amino, dialkylamino, alkylarylamino, diarylamino, alkoxy, cycloalkyl, aryloxy, alkenyl, cycloalkenyl, cyclohexadienyl, or alkyl, alkenyl, or aryl substituted with one or more halogen, cyano, nitro, mercapto, alkylthio or cyanomethylthio groups.

The compounds of this invention form basic salts with inorganic and organic bases. These salts are included within the language "pharmaceutically acceptable salts" and are within the scope of this invention. Such salts include ammonium salts, alkali metal salts, alkaline earth metal salts, and salts with organic bases such as dicyclohexylamine, benzathine, N-methyl-D-gluccamine, hydroamine and the like.

The term "prodrug" refers to any derivatives of compound I that would be metabolized to the active form of compound I. The free acid form of compound I (i.e., wherein Z is the open chain and R is hydrogen) is believed to be the active form. Some prodrugs thereof are comprised by symbols defining compound I; for example, wherein R is alkyl or wherein Z is the lactone. Other prodrugs may be readily prepared by those having ordinary skill in the art. See, for example, *Design of Prodrugs* edited by H. Bundgard (Elsevier 1985). All such prodrugs are within the scope of this invention.

Preferred Moieties

Preferred compounds of formula I are those wherein:
X is hydrogen or lithium;
Y is hydrogen or alkyl (methyl most preferred);

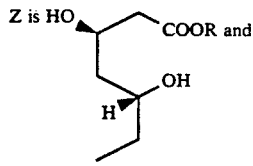

R is hydrogen or alkali metal (lithium most preferred).

Use and Utility

The compounds of formula I will be formulated with a pharmaceutical vehicle or diluent. The pharmaceutical composition can be formulated in a classical manner with solid or liquid vehicles or diluents and pharmaceutical additives appropriate to the desired mode of administration. The compounds can be administered by an oral route (e.g., tablets, capsules, granules or powders) or a parenteral route (e.g., injectable preparations).

A typical capsule for oral administration contains active ingredients (25 mg), lactose (75 mg) and magnesium stearate (15 mg). The mixture is passed through a 60-mesh sieve and packed into a No. 1 gelatin capsule.

A typical injectable preparation is produced by asceptically placing 25 mg of a water-soluble salt of sterile active ingredient into a vial, aseptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis. Such compounds are useful in treating atherosclerosis to inhibit progression of disease, in treating hyperlipidemia to inhibit development of atherosclerosis, and in treating nephrotic hyperlipidemia. In addition, the compounds of the invention increase plasma high density lipoprotein cholesterol levels. As HMG-CoA reductase inhibitors, the compounds of the invention may also be useful in inhibiting formation of gallstones and in treating tumors.

The compounds of the present invention may also be useful as anti-cancer agents by inhibiting the growth of tumors.

The compounds of the present invention may also be employed in combination with antihyperlipoproteinemic agents, such as probucol, and/or with one or more serum cholesterol lowering agents such as Lopid ® (gemfibrozil), bile acid sequestrants such as cholestyramine, colestipol, DEAE-Sephadex ® as well as clofibrate, nicotinic acid and its derivatives, neomycin, p-aminosalicylic acid, lovastatin, pravastatin, visinolin (velostatin, simvastatin or synvinolin) and the like, and/or one or more squalene synthetase inhibitors.

The above compounds to be employed in combination with the HMG-CoA reductase inhibitor of the invention will be used in amounts as indicated in the Physicians' Desk Reference (PDR).

The dose to be administered depends on the unitary dose, the symptoms, and the age and the body weight of the patient. A dose for adults is preferably between 20 and 2,000 mg per day, which can be administered in a single dose or in the form of individual divided doses from 1-4 times per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis*. For those utilities they are admixed with suitable formulating agents, powders, emulsifying agents or solvents (such as aqueous ethanol) and sprayed or dusted on the plants to be protected.

In addition, the compounds of the invention may also be useful in elevating HDL-cholesterol levels while lowering levels of LDL-cholesterol and serum triglycerides.

Process of Preparation

Compounds of formula I can be prepared by the following exemplary process.

Preparation of the compound

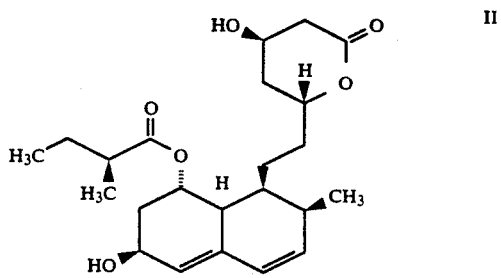

is described in U.S. Pat. Nos. 3,983,140 and 4,346,227. In the process of forming compound I, compound II is placed in an inert solvent (e.g., tetrahydrofuran or dichloromethane) under an inert atmosphere (e.g., argon or nitrogen) at a temperature of about 15° to 25° C. and treated with an appropriate silyl protecting agent (e.g., t-butyldimethylsilyl chloride, triethylsilyl chloride, or phenyldimethylsilyl chloride) in the presence of an appropriate amine base (e.g., imidazole) to form

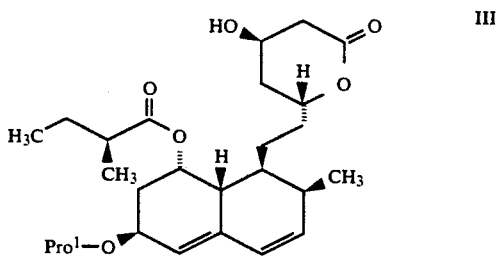

wherein Pro¹ is a silyl oxygen-protecting group such as

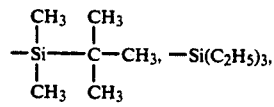

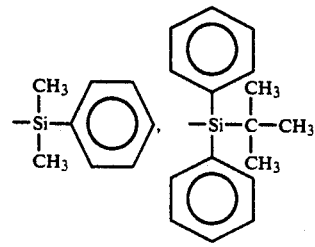

and the like.

Compound III is hydrogenated (e.g., with hydrogen gas) in an organic solvent (e.g., ethyl acetate) in the presence of a catalyst (e.g., platinum or carbon) to form a compound of the formula

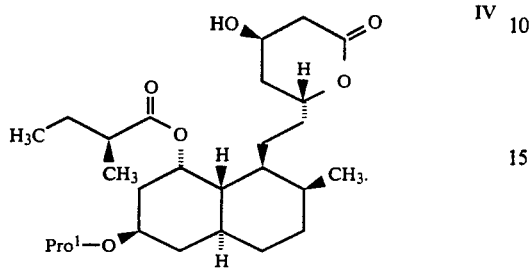

Compound IV is treated with a base (e.g., potassium hydroxide) in a mixture of water and an organic solvent such as toluene (optionally containing some methanol) to form the potassium salt

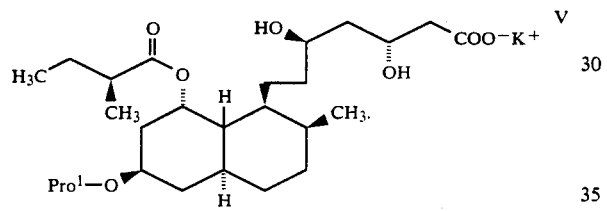

The potassium salt V is reacted in an organic solvent such as tetrahydrofuran with an organic base (e.g., pyrrolidine or piperidine) and n-butyllithium and an alkylating agent (e.g., iodomethane) in an inert atmosphere (e.g., argon) at about $-60°$ to $-20°$ C. (see European Patent Application 137,444). The resulting product is acidified, isolated and heated to about $100°-110°$ C. in an organic solvent (e.g., toluene) to form

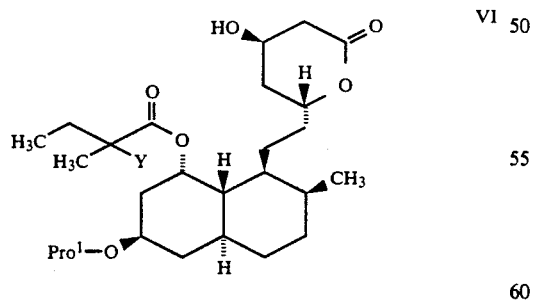

in which Y is alkyl.

Compound VI is oxygen-protected by, for example, reaction with a protecting agent (e.g., benzyl bromomethyl ether) in the presence of an amine base (e.g., N,N-dimethylaniline) in an organic solvent (e.g., methylene chloride) to form

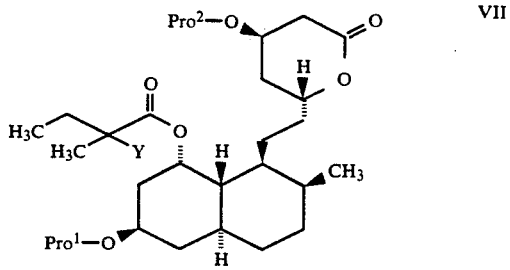

wherein $Pro^2$ is a different protecting group from $Pro^1$ and may be selected from benzyloxymethyl (which is preferred), p-methoxybenzyloxymethyl, tetrahydropyranyl, lower acyl and the like.

$Pro^1$ can then be removed by, for example, reaction with a deprotecting agent (e.g., hydrogen fluoride-pyridine) at about $-10°$ to $10°$ C. under an inert atmosphere (e.g., nitrogen) in an inert solvent (e.g., acetonitrile) to form

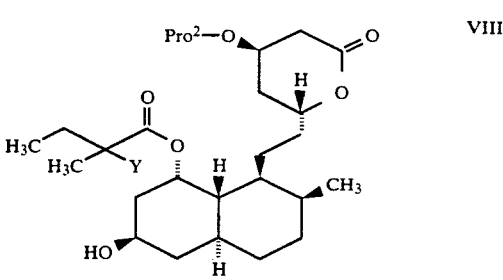

Monprotected diol VIII undergoes nucleophilic displacement by treatment with an alcohol activating complex (e.g., triphenylphosphine and diisopropyl azodicarboxylate), followed by a thio acid (e.g., thiolacetic acid) in an organic solvent (e.g., tetrahydrofuran) at about $-10°$ to $30°$ C. to form a thioacyl compound

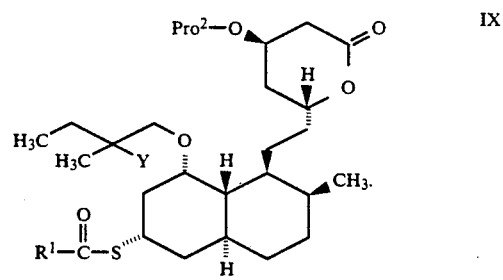

Compound IX's acyl group is oxidatively cleaved by treatment with an oxidant such as meta-chloroperoxybenzoic acid (m-CPBA) in water and an organic solvent (e.g., tetrahydrofuran) at about $-78°$ to $30°$ C. to form the associated sulfonic acid

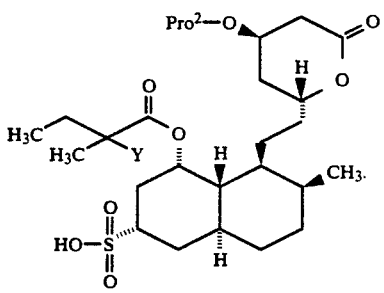

Compound X undergoes reductive cleavage and alcoholysis in an alcohol (e.g., methanol) in the presence of a catalyst (palladium hydroxide on carbon) with hydrogenation (H₂ balloon) at about 20° to 30° C. to form a dihydroxy acid ester compound of formula I wherein X is hydrogen, Z is the open chain and R is alkyl.

To form compound I wherein R and X are alkali metal, the ester is treated with an aqueous or ammonium base (e.g., lithium hydroxide) in an organic solvent or solvent mixture (e.g., methanol, tetrahydrofuran). R can be converted to hydrogen by treatment with a mild aqueous acid (e.g., potassium bisulfate).

To form compound I wherein n is 1, compound IX is treated with two equivalents of m-CPBA under the previously described conditions. The resulting sulfinic acid may then be stabilized by formation of the sodium salt under the above conditions.

The open chain acid compound I can be converted to the lactone by, for example, either heating in toluene to about 100° to 135° C. or treating with a catalytic amount of trifluoroacetic acid at about ambient temperature in an organic solvent (e.g., tetrahydrofuran).

The following working examples represent preferred embodiments of the invention and are illustrative rather than limiting. Unless otherwise specified, all temperatures are in degrees Celsius (°C.). The preparation of each compound appears below its name. As a shorthand reference, the compound prepared in part A will be called "Compound A" or "intermediate A" and so forth for all compounds hereafter.

EXAMPLE 1

[1S-[1α(βS*,ΔS*),2α,4aβ,6β,8β,8aα]]-8-(2,2-Dimethyl-1-oxobutoxy)decahydro-β,Δ-dihydroxy-2-methyl-6-sulfo-1-naphthaleneheptanoic acid, methyl ester

A.

[1S-[1α(R*),3β,4β,7β,8β(2S*,4S*),8aβ]]-2-Methylbutanoic acid, 3-[[(1,1-dimethylethyl)dimethylsilyl]oxy]-1,2,3,7,8,8a-hexahydro-7-methyl-8-[2-(tetrahydro-4-hydroxy-6-oxo-2H-pyran-2-yl)ethyl]-1- naphthalenyl ester The starting material for preparation of intermediate A was [1S-[1α(R*),3β,4β,7β,8β(2S*, 4S*),8aβ]]-2-methylbutanoic acid, 3-hydroxy-1,2, 3,7,8,8a-hexahydro-7-methyl-8-[2-(tetrahydro-4-hydroxy-6-oxo-2H-pyran-2-yl)ethyl]-1-naphthalenyl ester. Preparation of this starting material has been described in U.S. Pat. Nos. 3,983,140 and 4,346,227.

A solution of 8.43 g (20.7 mmol, 1.00 eq.) of the starting material in 80 ml of dry tetrahydrofuran under argon at ambient temperature was treated with 1.76 g (25.9 mmol, 1.25 eq.) of imidazole, followed by 3.44 g (22.8 mmol, 1.10 eq.) of t-butyldimethylsilyl chloride. A white precipitate formed almost immediately (5–10 sec). After stirring for 26 hours, the reaction mixture was diluted with 80 ml of ether, filtered and concentrated in vacuo. Purification of the residue by flash chromatography (with Merck silica gel; 40% ethyl acetate in hexanes) gave 7.41 g (a 69% yield) of the mono-silylated product (intermediate A) as a white solid, with a melting point of 111° to 115° C. More typical yields for this conversion are in the range of 80 to 85%. Lowering the temperature of the reaction or slowly adding a solution of t-butyldimethyl silyl chloride in tetrahydrofuran improves the yield somewhat.

B.

[1S-[1α(R*),3β,4aα,7β,8β(2S*,4S*),8aβ]]-2-Methylbutanoic acid,3-[[(1,1-dimethylethyl)dimethylsilyl]oxy]decahydro-7-methyl-8-[2-(tetrahydro-4-hydroxy-6-oxo-2H-pyran-2-yl)ethyl-1-naphthalenyl ester To a degassed, argon-purged solution of 9.38 g (18.0 mmol) of Compound A in 200 ml of ethyl acetate was added 1.4 g of 10% platinum on carbon. This suspension was subjected to 50 psi of H₂. A consumption of starting material resulted with generation of the desired product and some desilylated product. The filtered reaction mixture was concentrated and the products were isolated by flash chromatography. Elution with 45% hexanes in ethyl acetate gave 7.73 g (82%) of compound B as a clear glass and elution with 30% hexanes in ethyl acetate gave 0.98 g (13%) of desilylated product.

C.

[1S-[1α,3β,4aα,7β,8β(2S*,4S*),8aβ]]-2,2-Dimethylbutanoic acid,3-[[(1,1-dimethylethyl)dimethylsilyloxy]oxy]-decahydro-7-methyl-8-[2-(tetrahydro-4-hydroxy-6-oxo-2H-pyran-2-yl)ethyl]-1-naphthalenyl ester A solution of compound B (10.5 g, 20.04 mmol) in a mixture of toluene (200 mL) and methanol (42 mL) was treated with 1.0N potassium hydroxide (20 mL) at room temperature under an atmosphere of nitrogen for 45 minutes. The solvent was evaporated in vacuo to give a gum. This gum was azeotroped with benzene (250 mL) and then dried in vacuo at 45° (oil bath temperature) overnight to give a foamy solid.

To a chilled (−55°, acetonitrile-dry ice bath) and stirred solution of the above solid in dry tetrahydrofuran (150 mL) under an atmosphere of nitrogen was added dry pyrrolidine (6.48 mL, 77.63 mmol), followed by n-butyllithium (2.5M in hexane, 27.84 mL, 69.6 mmol). The mixture was gradually warmed up to −25° (carbon tetrachloride-dry ice bath) and stirred for 2.5 hours. Iodomethane (3.12 mL, 50.12 mmol) was added dropwise. After 1.0 hour, a small aliquot was worked up. ¹H-NMR spectrum indicated there was 15–20% non-methylated starting material present. Therefore, the mixture was recooled to −55°, more dry pyrrolidine (3.24 mL) and n-butyllithium (2.5M in hexane, 13.92 mL) were added, and the mixture was warmed up to −25°. After 2.5 hours, iodomethane (1.56 mL) was added and the mixture was stirred for another hour. The resulting mixture was quenched with 10% potassium bisulfate solution (100 mL) at −25°, warmed up to room temperature, saturated with sodium chloride and extracted with ethyl acetate (3×100 mL). The combined ethyl acetate extracts were washed with a small amount of 5% sodium bicarbonate and brine, dried over anhydrous sodium sulfate and evaporated in vacuo to give a gummy residue (11.0 g).

The above gum was refluxed in dry toluene (200 mL) under an atmosphere of nitrogen for 4.0 hours. The solvent was then evaporated in vacuo to give a gummy material. This gum was chromatographed on a column of silica gel (LPS-1, 450 g), eluting with ethyl acetate-hexane (1:3) to give 7.3 g (67.5%) of Compound C as a gum with consistent $^1$H-NMR and $^{13}$C-NMR spectra.

D.
[1S-[1α,3β,4aα,7β,8β(2S*,4S*),8aβ]]-2,2-Dimethylbutanoic acid,3-[[(1,1-dimethylethyl)dimethylsilyl]oxy]decahydro-7-methyl-8-[2-[tetrahydro-4-[(phenylmethoxy)methoxy]-6-oxo-2H-pyran-2-yl-ethyl]-1-naphthalenyl ester To a chilled (0°, ice bath) and stirred solution of Compound C (7.3 g, 13.52 mmol) in dry dichloromethane (80 mL) under an atmosphere of nitrogen was added dry N,N-dimethylaniline (3.7 g, 30.53 mmol). After 15 minutes, benzyl bromomethyl ether (5.62 g, 26.13 mmol) was added. The resulting solution was gradually warmed up to room temperature and stirred for 20 hours. The solvent was partially removed in vacuo. Ethyl acetate (300 mL) was added. The ethyl acetate solution was washed with a 10% potassium bisulfate solution, a saturated sodium bicarbonate solution and brine, dried over anhydrous sodium sulfate and evaporated in vacuo to give an oil. This oil was chromatographed on a column of silica gel (LPS-1, 300 g), eluting with ethyl acetate-hexane (1:9) to give 8.5 g (95.4%) of Compound D as an oil with consistent $^1$H-NMR and $^{13}$C-NMR spectra.

E. [1S-[1α,3β,4aα,7β,8β(2S*,4S*),8aβ]]-2,2-Dimethylbutanoic acid, 3-hydroxydecahydro-7-methyl-8-[2-[tetrahydro-4-[(phenylmethoxy)methoxy]-6-oxo-2H-pyran-2-yl]-ethyl]-1-naphthalenyl ester A solution of Compound D (8.5 g, 12.9 mmol) in dry acetonitrile (100 mL) was cooled to 0° (ice bath) under an atmosphere of nitrogen and treated with two 4 mL portions of hydrogen fluoridepyridine over 1.5 hours. The reaction mixture was diluted with ethyl acetate (200 mL), washed with a 10% potassium hydrogen sulfate solution, brine and a dilute sodium bicarbonate solution, dried over anhydrous sodium sulfate and evaporated in vacuo to give a gum. This gum was chromatographed on a column of silica gel (Baker 60-200 mesh, 300 g), eluting with ethyl acetate-hexane (35:65 and 1:1) to give 6.0 g (85.4%) of Compound E as a solid (m.p. 73-77°) with consistent $^1$H-NMR and $^{13}$C-NMR spectra.

F. 2,2-Dimethylbutanoic acid, [1S-[1α,3α,4aα,7β,8β(2S*,4S*),8aβ]]-3-(acetylthio)decahydro-7-methyl-8-[2-(tetrahydro-4-[(phenylmethoxy)methoxy]-6-oxo-2H-pyran-2-yl)ethyl]-1-naphthalenyl ester Diisopropyl azodicarboxylate (DIAD) (1.4 mL, 7.1 mmol) was added to a 0° C. solution of triphenylphosphine (1.896 g, 7.23 mmol) in anhydrous tetrahydrofuran (18 mL) under nitrogen. A light yellow precipitate began to form before all of the DIAD had been added. After stirring at 0° C. for 0.5 hours, a cold solution of compound E (1.969 g, 3.61 mmol) and thiolacetic acid (0.54 mL, 7.5 mmol) in tetrahydrofuran (9 mL) was added to the reaction over 10 minutes. The flask containing compound E was rinsed with tetrahydrofuran (2×1 mL). The reaction was stirred at 0° C. for 1.5 hours, then at room temperature for 2 hours. During the course of the warming, the reaction turned from a murky brown to a clear amber color. After 2 hours at room temperature, thin layer chromatography indicated that compound E had been consumed. The product was concentrated in vacuo, then chromatographed on silica gel eluting with 10% ethyl acetate in methylene chloride. Two additional chromatographies (same conditions as above) were required to obtain pure compound F (1.126 g, 1.87 mmol, 52%) as an oil. A second product, a mixture of alkenes resulting from dehydration of the alcohol in compound E, was obtained in 44% yield (0.840, 1.59 mmol). TLC: $R_f$=0.40 (silica gel; 10% ethyl acetate in methylene chloride; 15% phosphomolybdic acid in ethanol stain.

G. 2,2-Dimethylbutanoic acid, [1S-[1α,3α,4aα,7β,8β(2S*,4S*),8aβ]]-decahydro-7-methyl-3-sulfo-8-[2-[tetrahydro-6-oxo-4-[(phenylmethoxy)methoxy]-2H-pyran-2-yl]ethyl]-1-naphthalenyl ester To a solution of compound F (1.126 g, 1.87 mmol) in tetrahydrofuran (20 mL) was added water (0.40 mL, 22.4 mmol). The solution was cooled to −78° C., then meta-chloroperoxybenzoic acid (1.210 g of 80%, 5.61 mmol) was added and rinsed in with tetrahydrofuran (5 mL). After stirring for 3 hours at −78° C., thin layer chromatography indicated that some compound F was still present. After stirring for 18 hours at room temperature, thin layer chromatography indicated that all compound F had been consumed. Diluted the reaction with ether (20 mL) then added water (5 mL) and saturated sodium bisulfite (10 mL). The layers were separated and the organic layer washed with water (1×10 mL). The combined aqueous layers were extracted with ethyl acetate (3×10 mL) and the organic layers dried over magnesium sulfate. The ether layer contained benzoic acid plus a small amount of compound G (1.42 g). The ethyl acetate layer contained clean compound G by thin layer chromatography (0.848 g, 1.39 mmol, 74%). Compound G was chromatographed on silica gel eluting with 10% methanol, 0.5% acetic acid in methylene chloride. Concentrated product fractions were dried in vacuo for 18 hours to obtain sulfonic acid G, which contained some acetic acid (0.94 g).

TLC: $R_f$=0.20 (silica gel; 10:1:1 (methylene chloride/methanol/acetic acid); 15% phosphomolybdic acid in ethanol stain.

H.
[1S-[1α(βS*,ΔS*),2α,4aβ,6β,8β,8aα]]-8-(2,2-Dimethyl-1-oxobutoxy)decahydro-β,Δ-dihydroxy-2-methyl-6-sulfo-1-naphthaleneheptanoic acid, methyl ester To a solution of compound G (0.8297, 1.36 mmol) dissolved in methanol (10 mL) was added palladium hydroxide on carbon (0.10 g). The reaction flask was evacuated, and then H$_2$ was introduced via a balloon. The evacuation and H$_2$ introduction was repeated two more times. After 18 hours at room temperature, fresh palladium hydroxide on carbon (0.01 g) was added and hydrogenation continued. Two more portions of catalyst were added at 3-hour intervals, and the hydrogenation was continued for an additional 18 hours. Thin layer chromatography after this time indicated that compound G was present in about 50%. The reaction mixture was filtered through Celite ® and rinsed with methanol. The filtrate was concentrated to 10 mL, palladium hydroxide on carbon (0.01 g) was added and hydrogenated as before. Two more portions of catalyst were added at 3-hour intervals, and hydrogenation continued for 64 hours. After this time, thin layer chromatography indicated that most of compound G had reacted. The reaction mixture was filtered and rinsed as before, then concentrated in vacuo. The crude compound H (Example 1) was chromatographed on silica gel eluting with 15% methanol in methylene chloride. A portion (0.271 g) of desired product that contained some of compound G was resubjected to the hydrogenolysis conditions. After 18 hours, the reaction was worked up and chromatographed as above to yield Example 1 (0.1723 g, 0.33 mmol). The total combined yield of purified Example 1 from the reaction was 75%.

TLC: R$_f$=0.31 (silica gel; 7.8:1.1:1.1 methylene chloride/methanol/acetic acid); 15% phosphomolybdic acid in ethanol stain.

EXAMPLE 2

[1S-[1α(βS*,ΔS*),2α,4aβ,6β,8β,8aα]]-8-(2,2-Dimethyl-1-oxobutoxy)decahydro-β,Δ-dihydroxy-2-methyl-6-sulfo-1-naphthaleneheptanoic acid, dilithium salt To Example 1 (0.1723 g, 0.353 mmol) was added water (3 mL) and methanol (4 mL); not all of Example 1 would dissolve. 1N lithium hydroxide (0.883 mL, 0.883 mmol) was added, and then tetrahydrofuran (0.4 mL). After 2 hours at room temperature, a trace of Example 1 remained by thin layer chromatography. More lithium hydroxide (0.180 mL, 0.18 mmol) was added. After 0.5 hours at room temperature, some insoluble material was filtered off and the filtrate was concentrated in vacuo. The residue was chromatographed on CHP-20P, eluting with water (250 mL), 5% acetonitrile in water (500 mL) and then 20% acetonitrile in water (500 mL). Pure product eluted with 5% acetonitrile in water. Product fractions were combined and concentrated in vacuo. The residue was dissolved in water (10 mL), then filtered (Millipore, cellulose nitrate) and lyophilized to yield Example 2 (0.1378 g, 0.266 mmol) in 75%. Due to contamination with some unknown black particles, this material was rechromatographed as before on CHP-20P to yield Example 2.

TLC: R$_f$=0.23 (silica gel; 7:1.5:1.5 methylene chloride/methanol/acetic acid; 15% phosphomolybdic acid in ethanol stain.

Optical Rotation [α]$_D$= +63.6° (c=0.50, methanol)
Microanalysis for C$_{24}$H$_{40}$O$_9$S·2Li·3.8 H$_2$O: CalC'd: C 49.11; H 8.17; S 5.46, Found: C 49.11; H 7.84; S 5.43.

What is claimed is:

1. A compound of the formula wherein:
X is hydrogen, alkali metal or ammonium;
Y is hydrogen, alkyl, cycloalkyl, aryl, or aralkyl;

Z is

R is hydrogen, alkyl, ammonium, alkyl-ammonium, or alkali metal; n is 1 or 2
and wherein:
"alkyl" refers to straight and branched chain hydrocarbon groups of 1 to 12 carbon atoms that may be substituted with halo, hydroxy, thio, thio-alkyl, aryl, alkyl-aryl, haloaryl, cycloalkyl, or alkylcycloalkyl groups;
"aryl" and "ar" refer to monocyclic and bicyclic aromatic groups containing from 6 to 10 carbon atoms in the ring, which may be substituted with 1 or 2 lower alkyl groups, 1 to 5 halogen atoms, or 1 or 2 lower alkoxy groups; and
"cycloalkyl" refers to saturated cyclic hydrocarbon groups containing 3 to 12 carbon atoms and may be substituted with 1 or 2 halogens, 1 or 2 lower alkyl groups, or 1 or 2 lower alkoxy groups.

2. The compound of claim 1, wherein X is hydrogen or lithium.
3. The compound of claim 1, wherein Y is hydrogen or alkyl.
4. The compound of claim 1, wherein Y is methyl.
5. The compound of claim 1, wherein Z is 6. The compound of claim 1, wherein Z is and R is lithium.

7. The compound of claim 1 selected from the group consisting of:
[1S-[1α(βS*,ΔS*),2α,4aβ,6β,8β,8aα]]-8-(2,2-Dimethyl-1-oxobutoxy)decahydro-β,Δ-dihydroxy-2-methyl-6-sulfo-1-naphthaleneheptanoic acid, methyl ester; and
[1S-[1α(βS*,ΔS*),2α4aβ,6β,8β,8aα]]-8-(2,2-Dimethyl-1-oxobutoxy)decahydro-β,Δ-dihydroxy-2-methyl-6-sulfo-1-naphthaleneheptanoic acid, dilithium salt.

8. A hypocholesterolemic or hypolipidemic composition comprising a compound as defined in claim 1 and a pharmaceutically acceptable carrier therefor.

9. A combination comprising a compound as defined in claim 1 and an antihyperlipoproteinemic agent.

10. The combination as defined in claim 9 wherein the antihyperlipoproteinemic agent is probucol, gemfibrozil, a bile acid sequestrant, clofibrate, nicotinic acid, neomycin, p-aminosalicyclic acid or benzafibrate.

* * * * *